(12) United States Patent
Coffin et al.

(10) Patent No.: US 7,981,669 B2
(45) Date of Patent: Jul. 19, 2011

(54) VIRAL VECTORS

(75) Inventors: Robert S. Coffin, London (GB); Guy Richard Simpson, London (GB)

(73) Assignee: Biovex Limited, Oxford (GB)

( * ) Notice: Subject to any disclaimer, the term of this patent is extended or adjusted under 35 U.S.C. 154(b) by 0 days.

(21) Appl. No.: 11/339,804

(22) Filed: Jan. 25, 2006

(65) Prior Publication Data

US 2006/0188480 A1   Aug. 24, 2006

Related U.S. Application Data

(63) Continuation of application No. PCT/GB2004/003217, filed on Jul. 26, 2004.

(30) Foreign Application Priority Data

Jul. 25, 2003  (GB) .................................. 0317511.4

(51) Int. Cl.
| | |
|---|---|
| C12N 7/00 | (2006.01) |
| C12N 7/01 | (2006.01) |
| C12N 15/63 | (2006.01) |
| A61K 48/00 | (2006.01) |
| C12Q 1/00 | (2006.01) |
| C12Q 1/02 | (2006.01) |
| C12Q 1/70 | (2006.01) |
| G01N 33/567 | (2006.01) |

(52) U.S. Cl. ................. 435/320.1; 435/235.1; 435/91.4; 424/93.2

(58) Field of Classification Search .......................... None
See application file for complete search history.

(56) References Cited

U.S. PATENT DOCUMENTS

| | | | |
|---|---|---|---|
| 5,328,688 A | 7/1994 | Roizman | |
| 5,585,096 A | 12/1996 | Martuza et al. | |
| 5,824,318 A | 10/1998 | Mohr et al. | |
| 5,876,923 A | 3/1999 | Leopardi et al. | |
| 6,248,320 B1 | 6/2001 | Coffin et al. | |
| 6,284,289 B1 | 9/2001 | Van den Berghe | |
| 6,428,968 B1 | 8/2002 | Molnar-Kimber et al. | |
| 6,641,817 B1 | 11/2003 | Coffin et al. | |
| 6,713,067 B2 | 3/2004 | Coffin | |
| 6,719,982 B1 | 4/2004 | Coffin et al. | |
| 6,821,753 B2 | 11/2004 | Coffin | |
| 7,063,835 B2 | 6/2006 | Coffin et al. | |
| 7,118,755 B2 | 10/2006 | Coffin et al. | |
| 7,223,593 B2 | 5/2007 | Coffin et al. | |
| 7,537,924 B2 | 5/2009 | Coffin | |
| 2003/0040500 A1 | 2/2003 | Coffin | |
| 2003/0044384 A1 | 3/2003 | Roberts et al. | |
| 2003/0091537 A1 | 5/2003 | Coffin | |
| 2003/0113348 A1 | 6/2003 | Coffin | |
| 2003/0219409 A1 | 11/2003 | Coffin et al. | |
| 2004/0022812 A1 | 2/2004 | Coffin | |
| 2004/0063094 A1 | 4/2004 | Coffin et al. | |
| 2004/0219167 A1 | 11/2004 | Coffin | |
| 2005/0249707 A1 | 11/2005 | Coffin et al. | |
| 2006/0121522 A1 | 6/2006 | Coffin | |
| 2006/0188480 A1 | 8/2006 | Coffin et al. | |
| 2007/0003571 A1 | 1/2007 | Coffin | |
| 2007/0264282 A1 | 11/2007 | Coffin | |

FOREIGN PATENT DOCUMENTS

| | | |
|---|---|---|
| EP | 0828005 | 3/1998 |
| WO | 92/13943 A1 | 8/1992 |
| WO | WO-96/16164 | 5/1996 |
| WO | WO-97/04804 | 2/1997 |
| WO | 97/20935 A2 | 6/1997 |
| WO | WO-97/26904 | 7/1997 |
| WO | WO-98/04726 | 2/1998 |
| WO | WO-98/30707 | 7/1998 |
| WO | WO-98/37905 | 9/1998 |
| WO | WO-98/40492 A1 | 9/1998 |
| WO | WO-98/42855 | 10/1998 |
| WO | WO-98/51809 | 11/1998 |
| WO | WO-99/06583 A1 | 2/1999 |
| WO | WO-99/38955 | 8/1999 |
| WO | WO-99/60145 | 11/1999 |
| WO | WO-00/08191 | 2/2000 |
| WO | WO-00/08194 | 2/2000 |
| WO | WO-00/40734 | 7/2000 |
| WO | WO-00/75292 A1 | 12/2000 |
| WO | WO-01/46449 | 6/2001 |
| WO | WO-01/46450 | 6/2001 |
| WO | WO-01/53505 | 7/2001 |
| WO | WO-01/53506 | 7/2001 |
| WO | WO-01/53506 A2 | 7/2001 |
| WO | WO-01/53507 | 7/2001 |
| WO | WO-01/77358 | 10/2001 |
| WO | WO-2005/011715 | 2/2005 |

OTHER PUBLICATIONS

Liu et al. ICP34.5 deleted herpes simplex virus with enhanced oncolytic, immune stimulating, and anti-tumour properties. Gene Therapy, Feb. 2003, vol. 10, No. 4, pp. 292-303.*

Moriuchi et al. Double suicide gene therapy using a replication defective herpes simplex virus vector reveals reciprocal interference in a malignant glioma model. Gene Therapy, May 2002, vol. 9, No. 9, pp. 584-591.*

(Continued)

*Primary Examiner* — Bao Li

(74) *Attorney, Agent, or Firm* — Fulbright & Jaworski L.L.P.

(57) ABSTRACT

The present invention provides a herpes virus which lacks a functional ICP34.5 encoding gene and which comprises two or more of—(i) a gene encoding a prodrug converting enzyme; (ii) a gene encoding a protein capable of causing cell to cell fusion; and (iii) a gene encoding an immunomodulatory protein.

12 Claims, 12 Drawing Sheets

OTHER PUBLICATIONS

Galanis et al. Use of viral fusogenic membrane glycoproteins as novel therapeutic transgenes in gliomas. Human Gene Therapy, May 2001, vol. 12, No. 7, pp. 811-821.*

Jones et al. Mutational Analysis of the herpes simplex virus virus virions host shutoff protein; evidence that vhs functions in the absence of other viral proteins. Journal of Virology, Aug. 1995, vol. 69, No. 8, pp. 4862-4871.*

Cassady et al. Journal of Virology, Nov. 1998, vol. 72, No. 11, pp. 8620-8626. especially Abstract.*

Varghese et al. Cancer Gene Therapy, Dec. 2002, vol. 9, No. 12, pp. 967-978.*

International Search Report for PCT International No. PCT/GB2004/003217.

Fu, Xinping, et al.; Expression of a Fusogenic Membrane Glycoprotein by an Oncolytic Herpes Simplex Virus Potentiates the Viral Antitumor Effect; Molecular Therapy 7(6):748-754, Jun. 2003.

Andreansky et al., "Evaluation of genetically engineered herpes simplex viruses as oncolytic agents for human malignant brain tumors," *Cancer Res.*, 57(8): 1502-1509, 1997.

Andreansky et al., "The application of genetically engineered herpes simplex viruses to the treatment of experimental brain tumors," *Proc. Nat. Acad. Sci. USA*, 93: 11313-11318, 1996.

Andreansky et al., "Treatment of intracranial gliomas in immunocompetent mice using herpes simplex viruses that express murine interleukins," *Gene Therapy*, 5: 121-130, 1998.

Bateman et al., "Fusogenic membrane glycoproteins as a novel class of genes for the local and immune-mediated control of tumor growth," *Cancer Res.*, 60: 1492-1497, 2000.

Broberg et al., "Expression of interleukin-4 but not of interleukin-10 form a replicative herpes simplex virus type 1 viral vector precludes experimental allergic encephalomyelitis," *Gene Therapy*, 8: 769-777, 2001.

Bronte et al., "IL-2 enhances the function of recombination poxvirus-based vaccines in the treatment of established pulmonary metastases," *J. Immunol.*, 154: 5282-5292, 1995.

Chambers et al., "Comparison of genetically engineered herpes simplex viruses for the treatment of brain tumors in a *scid* mouse model of human malignant glioma," *Proc. Natl. Acad. Sci. USA*, 92(5): 1411-1415, 1995.

Chou et al., "Mapping of herpes simplex virus-1 neurovirulence to γ34.5, a gene nonessential for growth in culture," *Science*, 250: 1262-1266, 1990.

Coukos et al., "Oncolytic herpes simplex virus-1 lacking ICP34.5 induces p53 independent death and is efficacious against chemotherapy-resistant ovarian cancer," *Clin. Cancer Res.*, 6: 3342-3353, 2000.

Coukos et al., "Producer cells enhance the oncolytic effect of a replication-competent ICP34.5-null herpes simplex virus-1 (HSV-1) strain in epithelial ovarian cancer," *Cancer Gene Ther.*, 5(6): S7, 1998.

Coukos et al., "Use of carrier cells to deliver a replication selective herpes simplex virus-1 mutant for the intrapetioneal therapy of epithelial ovarian cancer," *Clin. Cancer Res.*, 5: 1523-1537, 1999.

Dranoff et al., "Vaccination with irradiated tumor cells engineered to secrete murine granulocyte-macrophage colony-stimulating factor stimulates potent, specific and long-lasting anti-tumor immunity," *Proc. Natl. Acad. Sci. USA*, 90: 3539-3543, 1993.

Ejercito et al., "Characterization of herpes simplex virus strains differing in their effects on social behaviour of infected cells," *J. Gen. Virol.*, 2: 357-364, 1968.

Ezzeddine et al., "Selective killing of glioma cells in culture and in vivo by retrovirus transfer of the herpes simplex virus thymidine kinase gene," *The New Biologist*, 3(6): 608-614, 1991.

Fulci et al., "Oncolytic viruses for the therapy of brain tumors and other solid malignancies: a review," *Frontiers in Bioscience*, 8: e346-360, 2003.

Galanis et al., "Use of viral fusogenic membrane glycoproteins as novel therapeutic transgenes in gliomas," *Human Gene Therapy*, 12: 811-821, 2001.

Goldsmith et al., "Infected cell protein (ICP)47 enhances herpes simplex virus neurovirulence by blocking the CD8+ T cell response," *J. Exp. Med.*, 187(3): 341-348, 1998.

Gossen et al., "Tight control of gene expression in mammalian cells by tetracycline-repsonsive promoters," *Proc. Natl. Acad. Sci. USA*, 89: 5547-5551, 1992.

Gossen et al., "Transcriptional activation by tetracyclines in mammalian cells," *Science*, 268: 1766-1769, 1995.

He et al., "Suppression of the phenotype of $_{\gamma 1}$34.5 herpes simplex virus 1: failure of activated RNA-dependent protein kinase to shut off protein synthesis is associated with a deletion in the domain of the α47 gene," *J. Virology*, 71(8): 6049-6054, 1997.

Hill et al., "Herpes simplex virus turns off the TAP to evade host immunity," *Nature*, 375: 411-415, 1995.

Hunter et al., "Attenuated, replication-competent herpes simplex virus type 1 mutant G207: safety evaluation of intracerebral injection in nonhuman primates," *J. Virol.*, 73(8): 6319-6326, 1999.

Irvine et al., "Cytokine enhancement of DNA immunization leads to effective treatment of established pulmonary metastases," *J. Immunol.*, 156: 238-245, 1996.

Krisky et al., "Development of herpes simplex virus replication-defective multigene vectors for combination gene therapy applications," *Gene Therapy*, 5(11): 1517-1530, 1998.

Lachmann et al., "Gene transfer with herpes simplex vectors," *Curr. Opin. Mol. Ther.*, 1(5): 622-632, 1999.

Liu et al., "ICP34.5 deleted herpes simplex virus with enhanced oncolytic, immune stimulating and anti-tumour properties," *Gene Ther.*, 10: 292-303, 2003.

Maclean et al., "Herpes simplex virus type 1 deletion variants 1714 and 1716 pinpoint neurovirulence-related sequences in Glasgow strain 17+ between immediate early gene 1 and the 'a' sequence," *J. Gen. Virol.*, 72: 631-639, 1991.

Markert et al., "Reduction and elimination of encephalitis in an experimental glioma therapy model with attenuated herpes simplex mutants that retain susceptibility to acyclovir," *Neurosurgery*, 32: 597-604, 1993.

Martuza et al., "Experimental therapy of human glioma by means of a genetically engineered virus mutant," *Science*, 252: 854-856, 1991.

McKie et al., "Selective in vitro replication of herpes simplex virus type 1 (HSV-1) ICP34.5 null mutants in primary human CNS tumours—evaluation of a potentially effective clinical therapy," *Br. J. Cancer*, 74: 745-752, 1996.

Meignier et al., "In vivo behaviour of genetically engineered herpes simplex viruses R7017 and R7020: construction and evaluation in rodents," *J. Infect. Dis.*, 158(3): 602-614, 1988.

Moriuchi et al., "Enhanced tumor cell killing in the presence of ganciclovir by herpes simplex virus type 1 vector-directed coexpression of human tumor necrosis factor-alpha and herpes simplex virus thymidine kinase," *Cancer Res.*, 58(24): 5731-5737, 1998.

Mullen et al., "Viral Oncolysis," *The Oncologist*, 7: 106-119, 2002.

Parker et al., "Engineered herpes simplex virus expressing IL-12 in the treatment of experimental brain tumors," *Proc. Natl. Acad. Sci. USA*, 97(5): 2208-2213, 2000.

Randazzo et al., "Herpes simplex 1716 an ICP 34.5 mutant is severely replication restricted in human skin xenografts in vivo," *Virology*, 223(2): 392-395, 1996.

Rekabdar et al., "Variability of the glycoprotein G gene in clinical isolates of herpes simplex virus type 1," *Clin. Diag. Lab. Immunol.*, 6(6): 826-831, 1999.

Shi et al., "Granulocyte-macrophage colony-stimulating factor (GM-CSF) secreted by cDNA-transfected tumor cells induces a more potent antitumor response than exogenous GM-CSF," *Cancer Gene Ther.*, 6(1): 81-88, 1999.

Speck et al., "In Vivo complementation studies of a glycoprotein H-deleted herpes simplex virus-based vector," *J. Gen. Virol.*, 77(10): 2563-2568, 1996.

Thompson et al., "DNA sequence and RNA transcription through a site of recombination in a non-neurovirulent herpes simplex virus intertypic recombinant," *Virus Genes*, 1(3): 275-286, 1998.

Toda et al., "*In situ* cancer vaccination: an IL-12 defective vector/replication-competent herpes simplex virus combination induces local and systemic antitumor activity," *J. Immunol.*, 160: 4457-4464, 1998.

Toyoizumi et al., "Combination therapy with herpes simplex virus type 1 ICP34.5 mutant (HSV-1716) and common chemotherapeutic agents for human non-small cell lung cancer (NSCLS)," Cancer Gene Ther., 5(6): S7-8, 1998.

Simpson, et al., "Combination of a Fusogenic Glycoprotein, Prodrug Activation, and Oncolytic Herpes Simplex Virus for Enhanced Local Tumor Control," Cancer Res 2006; 66:(9).May 1, 2006.

Hu et al. (2006), "A phase I study of OncoVex$^{GM-CSF}$, a second generation oncolytic herpes simplex virus expressing granulocyte macrophage colony-stimulating factor", Clinical Cancer Research 12, 6737-6747.

Diaz et al. et al., "A lentiviral vector expressing a fusogenic glycoprotein for cancer gene therapy", (2000) Gene Ther. 7:1656-63.

Galanis et al.; "Use of Viral Fusogenic Membrane Glycoproteins as Novel Therapeutic Transgenes in Gliomas"; Human Gene Therapy; May 2001; vol. 12, No. 7, pp. 811-821.

Jones et al.; "Mutational Analysis of the Herpes Simplex Virus Virion Host Shutoff Protein: Evidence that VHS Functions in the Absence of Other Viral Proteins"; Journal of Virology; Aug. 1995; vol. 69, No. 8, pp. 4862-4871.

Mullen et al., "Transfer of the bacterial gene for cytosine deaminase to mammalian cells confers lethal sensitivity to 5-fluorocytosine: A negative selection system"; 1992, PNAS 89:33-37.

Simpson et al., "Combination of a Fusogenic Glycoprotein, Prodrug Activation, and Oncolytic Herpes Simplex Virus for Enhanced Local Tumor Control"; (2006) Cancer Res. 66:4835-4842.

Varghese et al., "Oncolytic Herpes Simplex Virus Vectors for Cancer Virotherapy"; Cancer Gene Therapy, Dec. 2002, vol. 9, No. 12, pp. 967-958.

Ace et al.; "Construction and Characterization of a Herpes Simplex Virus Type 1 Mutant Unable to Transinduce Immediate Early Gene Expression"; 1989; J. Virology 63:2260-2269.

Bowie et al.; "Deciphering the Message in Protein Sequences: Tolerance to Amino Acid Substitutions"; Science; Mar. 1990; 16:247(4948):1306-10.

Chou et al.; Differential Response of Human Cells to Deletions and Stop Codons in the Y134.5 Gene of Herpes Simplex Virus; Journal of Virology, pp. 8304-8311 (Dec. 1994).

Chou et al.; "The Y134.5 Gene of Herpes Simplex Virus 1 Precludes Neuroblastoma Cells From Triggering Total Shutoff of Protein Synthesis Characteristic of Programmed Cell Death in Neuronal Cells"; Proc. Natl. Acad. Sci. vol. 89, pp. 3266-3270 (Apr. 1992).

DeLuca et al.; "Isolation and Characterization of Deletion of Mutants of Herpes Simplex Virus Type 1 in The Gene Encoding Immediate-Early Regulatory Protein ICP4"; J. Virology 1985; vol. 56:558-570.

Howard et al.; "High Efficiency Gene Transfer to the Central Nervous System of Rodents and Primates Using Herpes Virus Vectors Lacking Functional ICP27 and ICP34.5"; Gene Therapy 1998; vol. 5:1137-1147.

Krisky et al.; "Deletion of Multiple Immediate-Early Genes from Herpes Simplex Virus Reduces Cytotoxicity and Permits Long-Term Gene Expression in Neurons"; 1998; Gene Therapy; 5:1593-1603.

McFarlane et al.; "Hexamethylene Bisacetamide Stimulates Herpes Simplex Virus Immediate Early Gene Expression in the Absence of Trans-Induction by Vmw65"; 1992; J. Gen. Virology 73:285-292.

Rice et al.; "Genetic Evidence for Two Distinct Transactivation Functions of the Herpes Simplex Virus & Protein ICP27"; 1990; J. Virology 64:1704-1715.

Samaniego et al.; "Functional Interactions Between Herpes Simplex Virus Immediate-Early Proteins During Infection: Gene Expression as a Consequence of ICP27 and Different Domains of ICP4"; 1995; J. Virology 69:5705-5715.

Samaniego et al.; "Persistence and Expression of the Herpes Simplex Virus Genome in the Absence of Immediate-Early Proteins"; 1998; J. Virology 72:3307-3320.

Smiley et al.; "Truncation of the C-Terminal Acidic Transcriptional Activation Domain of Herpes Simplex Virus VP16 Produces a Phenotype Similiar to that of the in 1814 Linker Insertion Mutation"; 1997; J. Virology 71:6191-6193.

Smith et al.; "Evidence that the Herpes Simplex Virus Immediate Early Protein ICP27 Acts Post-Transcriptionally During Infection to Regulate Gene Expression"; 1992; Virology 186:74-86.

Thomas et al.; "Herpes Simplex Virus Latency-Associated Transcript Encodes a Protein Which Greatly Enhances Virus Growth, Can Compensate for Deficiencies in Immediate-Early Gene Expression, and is Likely to Function During Reactivation from Virus Latency"; 1999; J. Virology 73:6618-6625.

Todryk et al.; 1999; Human Gene Therapy; vol. 10(17); pp. 2757-2768.

Zhu, Jia et al.; "Identification of a Novel 0.7-kb Polyadenylated Transcript in the LAT Promoter Region of HSV-1 That is Strain Specific and May Contribute to Virulence"; Virology 265; pp. 296-307; Oct. 15, 1999; Article ID viro. 1999.0057 (available online at http://www.idealibrary.com).

* cited by examiner

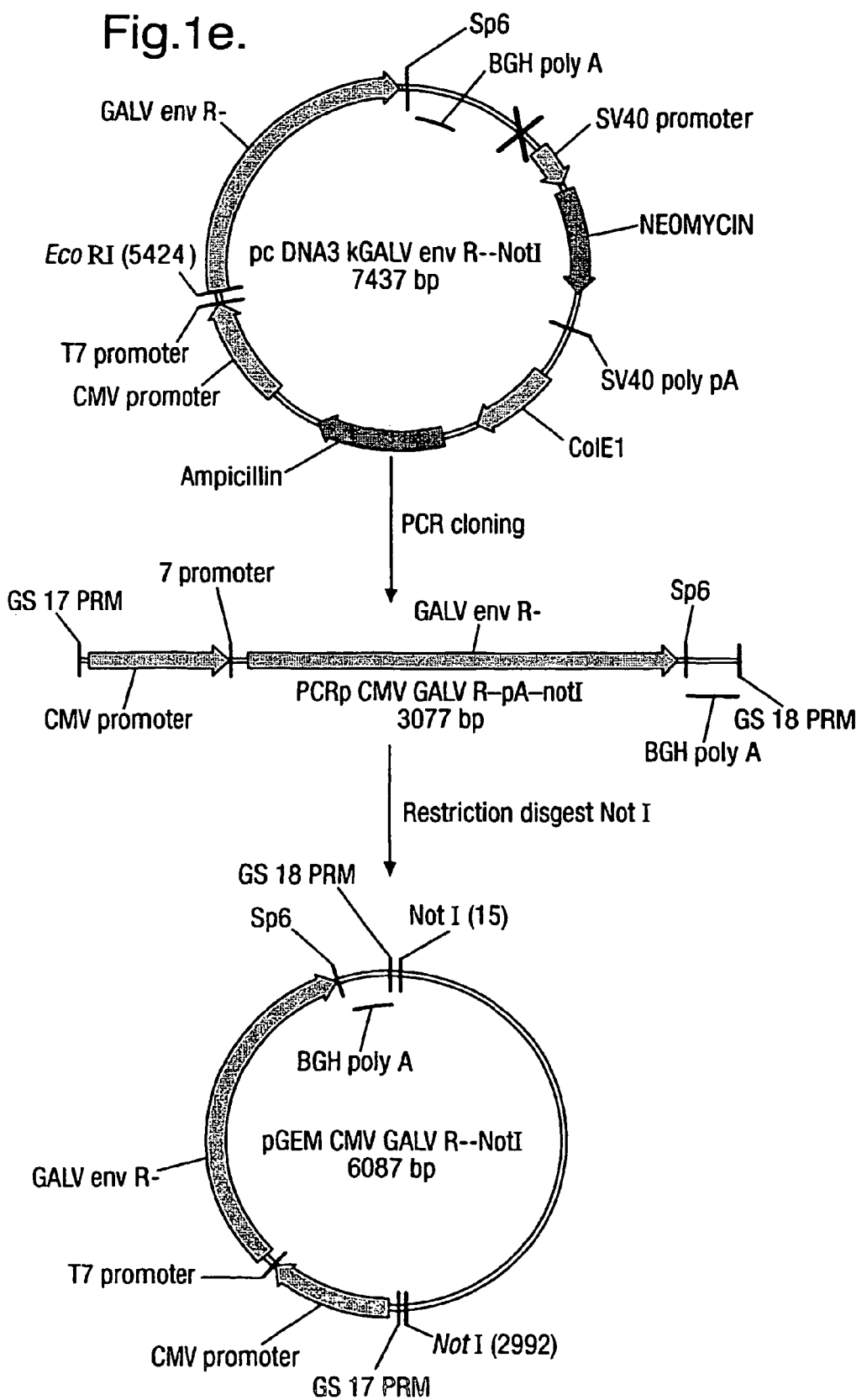

VIRAL VECTORS

This is a continuation of International Application Number PCT/GB2004/003217 (WO2005/011715) filed Jul. 26, 2004, which claims priority to United Kingdom Application Number 0317511.4 filed Jul. 25, 2003, this application claims priority to each of the above-referenced applications and each are incorporated herein by reference in their entireties.

FIELD OF THE INVENTION

The present invention relates to herpes virus strains with improved anti-tumour activity as compared to previously known strains.

BACKGROUND TO THE INVENTION

Viruses have been shown to have utility in a variety of applications in biotechnology and medicine on many occasions. Each is due to the unique ability of viruses to enter cells at high efficiency. This is followed in such applications by either virus gene expression and replication and/or expression of an inserted heterologous gene. Thus viruses can either deliver and express viral or other genes in cells which may be useful in for example gene therapy or the development of vaccines, or they may be useful in selectively killing cells by lytic replication or the action of a delivered gene in for example cancer.

Herpes simplex virus (HSV) has been suggested to be of use for the oncolytic treatment of cancer. A virus for use in treating cancer must however be disabled such that it is no longer pathogenic, i.e. does not replicate in and kill non-tumor cells, but such that it can still enter and kill tumor cells. For the oncolytic treatment of cancer, which may also include the delivery of gene(s) enhancing the therapeutic effect, a number of mutations to HSV have been identified which still allow the virus to replicate in culture or in actively dividing cells in vivo (e.g. in tumors), but which prevent significant replication in normal tissue. Such mutations include disruption of the genes encoding ICP34.5, ICP6 and thymidine kinase. Of these, viruses with mutations to ICP34.5, or ICP34.5 together with mutation of, for example, ICP6, have so far shown the most favourable safety profile. Viruses deleted only for the neurovirulence factor ICP34.5 have been shown to replicate in many tumor cell types in vitro and to selectively replicate in artificially induced brain tumors in mice while sparing surrounding tissue. Early stage clinical trials have also shown their safety in man.

SUMMARY OF THE INVENTION

The present invention provides viruses with improved capabilities for the destruction of tumor cells in vivo. Viruses provided by the present invention comprise an inactivating mutation in the gene encoding ICP34.5 and are capable of delivering two genes which, in combination, enhance the therapeutic effect. The virus comprises a gene from two or more of the following types:

A gene which encodes a pro-drug activating enzyme capable of converting an inactive or poorly active prodrug into the active or more active form. Treatment of tumors with the virus is therefore accompanied by administration of the prodrug.

A gene which encodes a protein capable of fusing cells (ie causing the formation of syncytia). This itself provides anti-tumour effect, which may be mediated by the induction of an immune response. However, in combination with pro-drug activation this anti-tumour effect is enhanced. Such fusogenic genes include modified retroviral envelope glycoproteins such as those derived from gibbon ape leukaemia virus or human endogenous retrovirus W, the fusogenic F and H proteins from measles virus or the vesicular stomatitis virus G protein, but other genes encoding proteins capable of causing cell fusion may also be used.

A gene which encodes an immunomodulatory protein. The immunomodulatory protein promotes an anti-tumour immune response. Such gene(s) include immune modulators such as GM-CSF, TNFα, CD40L or other cytokines or co-stimulatory molecules. The immunomodulatory protein enhances the effects of the prodrug activating gene and/or the protein capable of causing cell to cell fusion alone. Thus, viruses of the invention include viruses encoding a prodrug activating gene and an immunomodulatory gene, but no protein capable of causing cell to cell fusion, and viruses encoding a protein capable of causing cell to cell fusion and an immunomodulatory gene, but no prodrug converting gene.

The present invention thus provides viruses capable of the oncolytic destruction of tumor cells in which, when administered to a patient, optionally in combination with a prodrug, the anti-tumor properties of the virus are enhanced by the combined actions of the activated prodrug and the fusogenic and/or immunomodulatory protein expressed from the viral genome, or by the combined actions of the fusogenic protein and the immunomodulatory protein expressed from the viral genome.

Accordingly, the invention provides:
a herpes virus which lacks a functional ICP34.5 encoding gene and which comprises two or more of:
  (i) a gene encoding a prodrug converting enzyme;
  (ii) a gene encoding a protein capable of causing cell to cell fusion; and
  (iii) a gene encoding an immunomodulatory protein.

Preferably the herpes virus is one which lacks a functional ICP34.5 encoding gene and which comprises:
  (i) a gene encoding a prodrug converting enzyme; and
  (ii) a gene encoding a protein capable of causing cell to cell fusion.

The invention also provides:
  a herpes virus of the invention for use in a method of treatment of the human or animal body by therapy.
  use of a herpes virus of the invention in the manufacture of a medicament for the treatment of cancer.
  a pharmaceutical composition comprising as active ingredient a herpes virus according to the invention and a pharmaceutically acceptable carrier or diluent.
  a method of treating a tumour in an individual in need thereof by administering to said individual an effective amount of a herpes virus according to the invention.

BRIEF DESCRIPTION OF THE DRAWINGS

FIG. 1 depicts the plasmids used to construct the viruses of the invention and illustrates how the plasmids were constructed. The plasmids encode either a cytosine deaminase gene or a gibbon ape leukemia (GALV) fusogenic glycoprotein, or both genes flanked by HSV1 sequences flanking the ICP34.5 encoding gene. The plasmids can be used for homologous recombination into the HSV1 gene to replace the ICP34.5 encoding gene with either the cytosine deaminase gene, the GALV glycoprotein gene or both genes. These plasmids were then used to construct the viruses shown in FIG. 2.

FIG. 1e shows the subcloning of GALV env R− virus (Genbank NC 001885, 5552-7555 bp) from pcDNA3 (Invitrogen) to pGEM T Easy by PCR (Promega).

DETAILED DESCRIPTION OF THE INVENTION

A. Viruses

Figure 1A:
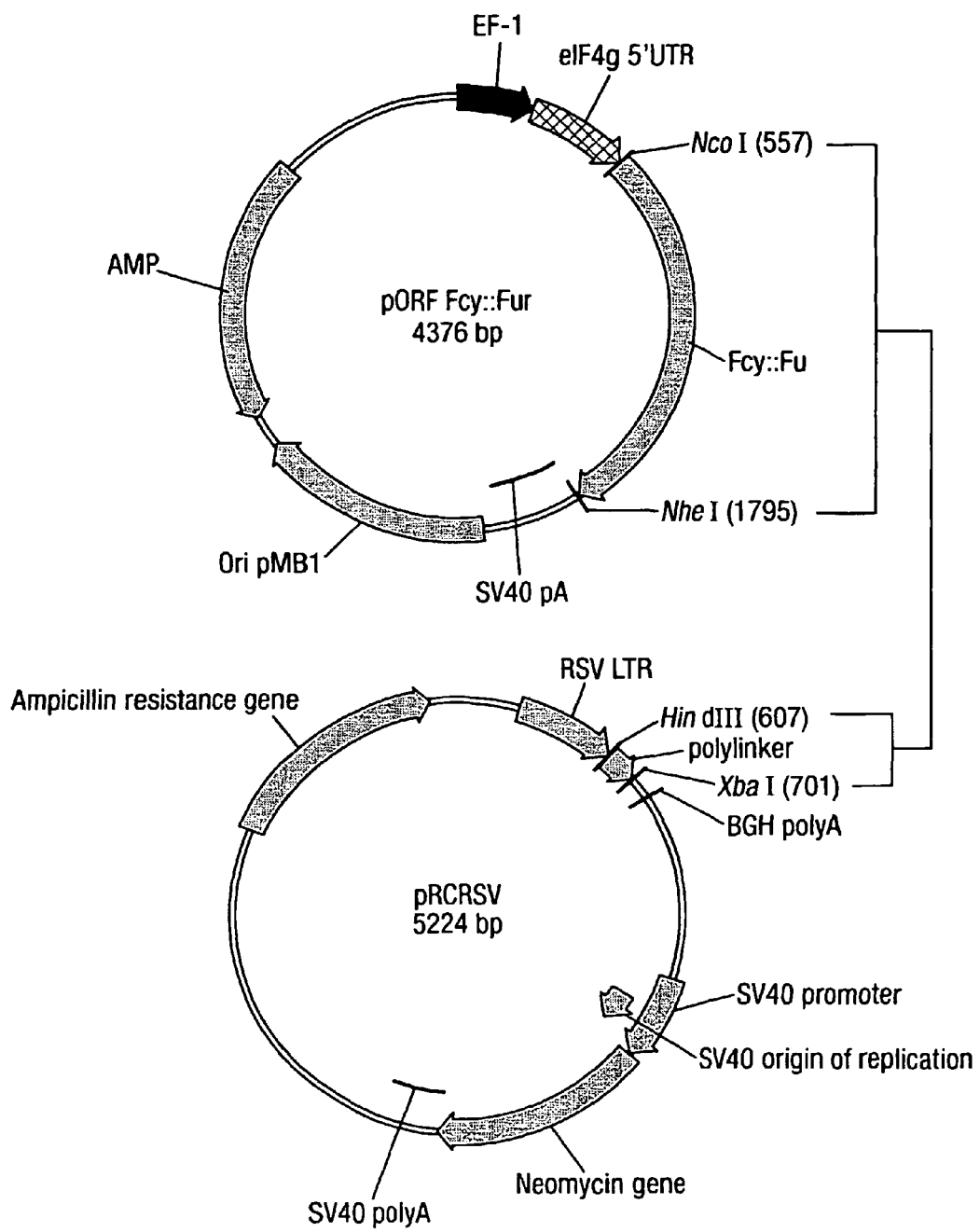
FIG. 1a shows the subcloning of Fcy:Fur gene from pORF Fcy:Fur (Invivogen) to pRcRSV (Invitrogen). Fcy:Fur gene was removed by restriction digestion (Nhe I and Nco I (blunted with T⁴ polymerase). This fragment was then ligated into pRcRSV (Invitrogen) cut with Xba I and Hind III (blunted with T⁴ polymerase).
Figure 1B:
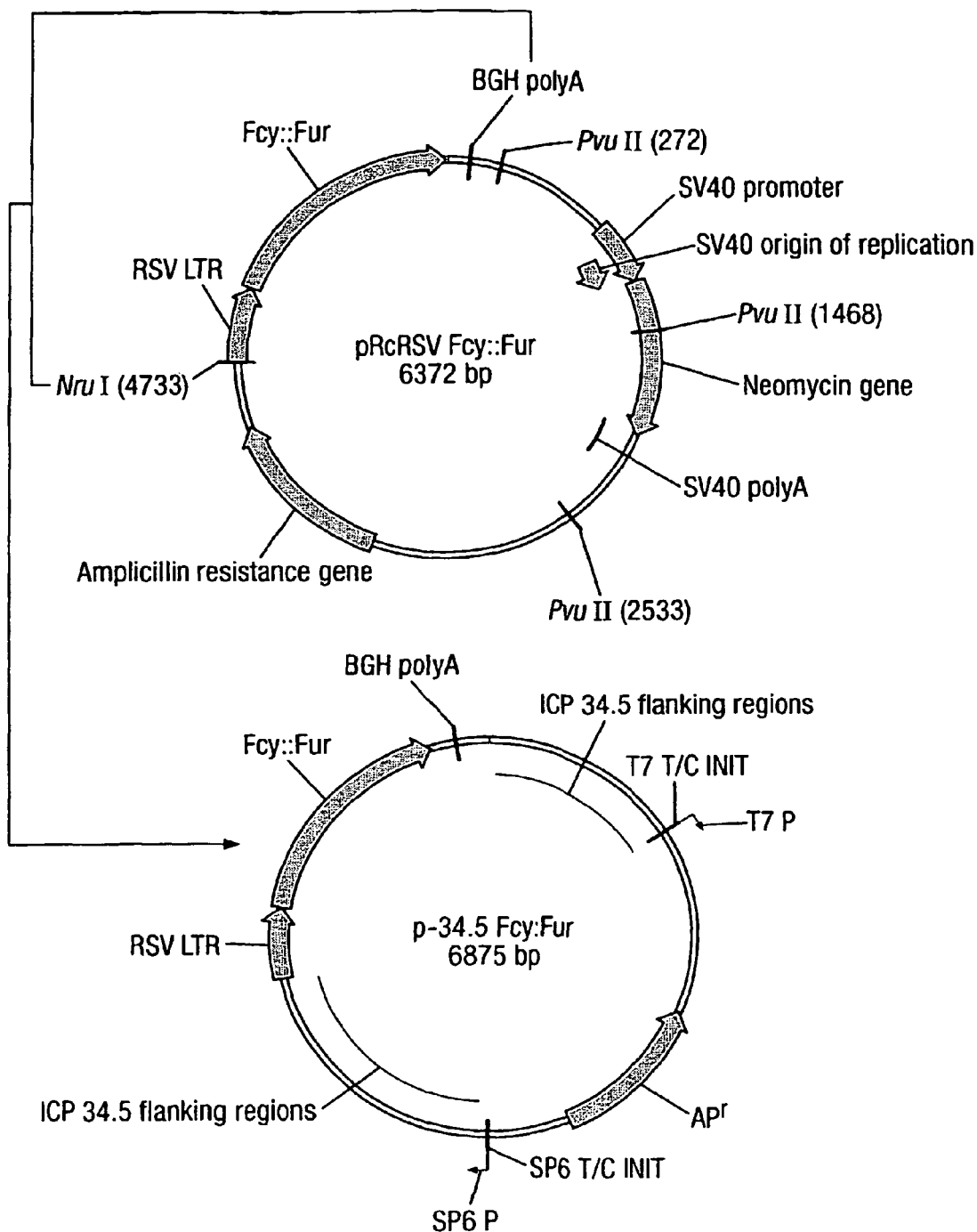
FIG. 1b shows the subcloning of RSV Fcy:Fur pA cassette from pRcRSV into p-34.5 by restriction digestion (Pvu II, NruI). This fragment was then ligated into the shuttle vector p-34.5 cut with NotI (blunted with T⁴ polymerase). p-34.5 plasmid is based on pSP72 (Promega) and contains two flanking regions either side of HSV-1 ICP34.5 gene (based on HSV-117+strain (123462-124958 bp, 125713-126790 bp)) Genbank X14112).
Figure 1C:
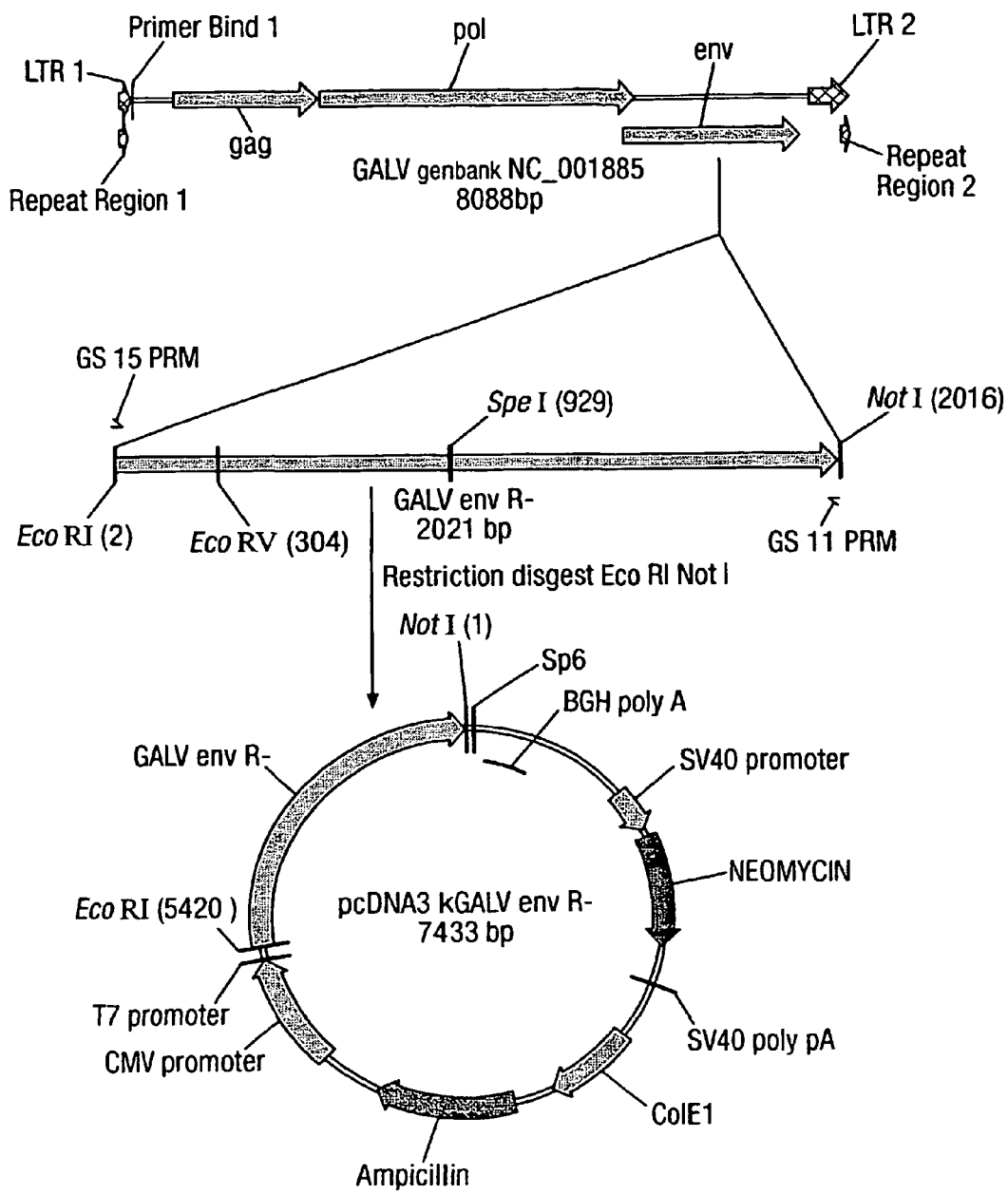
FIG. 1c shows the truncated envelope (env) of Gibbon Ape Leukaemia virus (Genbank NC_001885, 5552-7555 bp) which was obtained by RT-PCR from a viral producer cell line (MLV 144, Rangan et al., 1979). The envelope (GALV env R−) was cloned into pcDNA3 (Invitrogen) (by restriction disgested Eco RI Not I), a mammalian expression vector and three of the clones were tested for syncytia production.
Figure 1D:
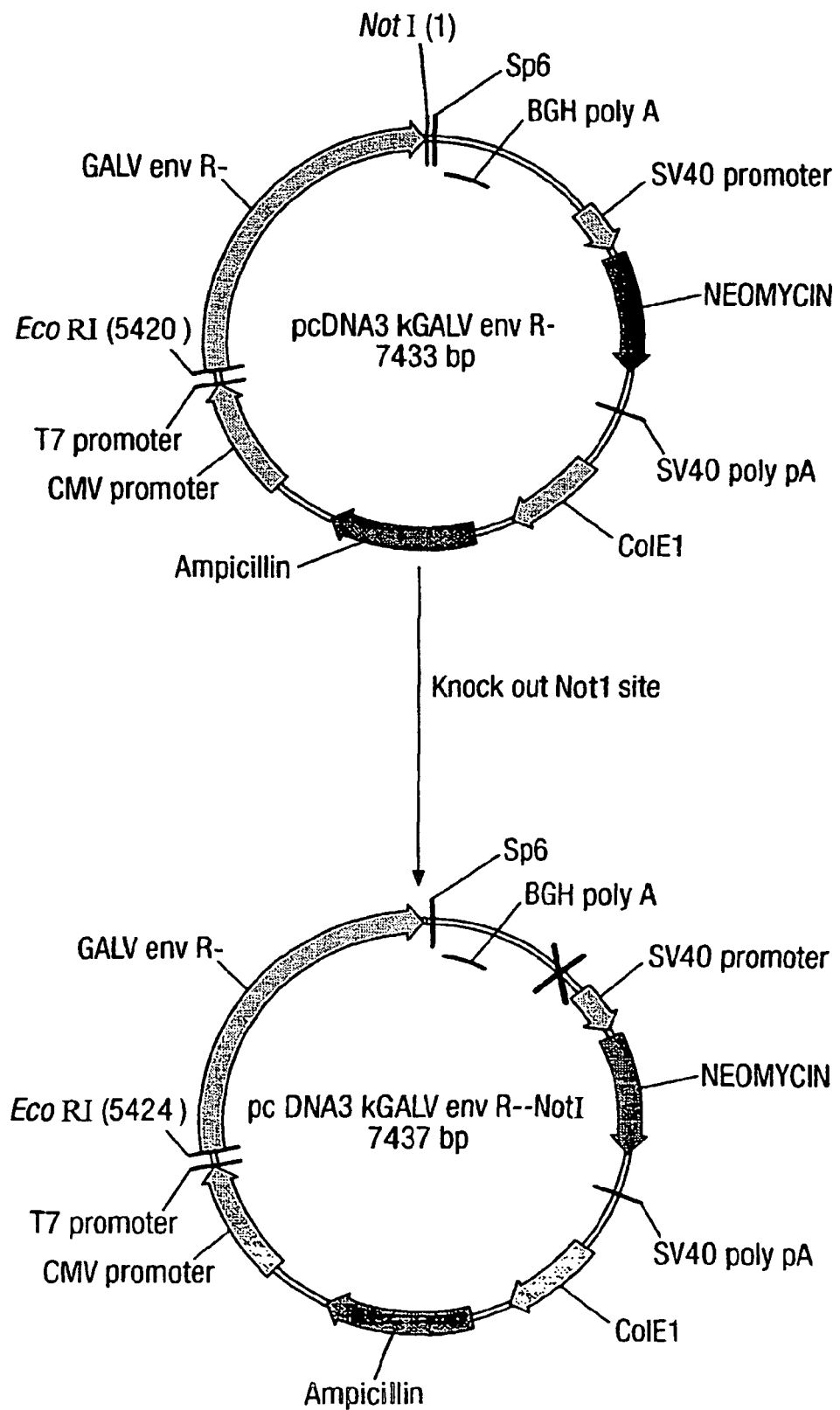
FIG. 1d shows the knock out of a Not-1 site in pcDNA3 GALV env R− by digestion using Not I and blunted with T⁴ polymerase, follow by religation.
Figure 1F:
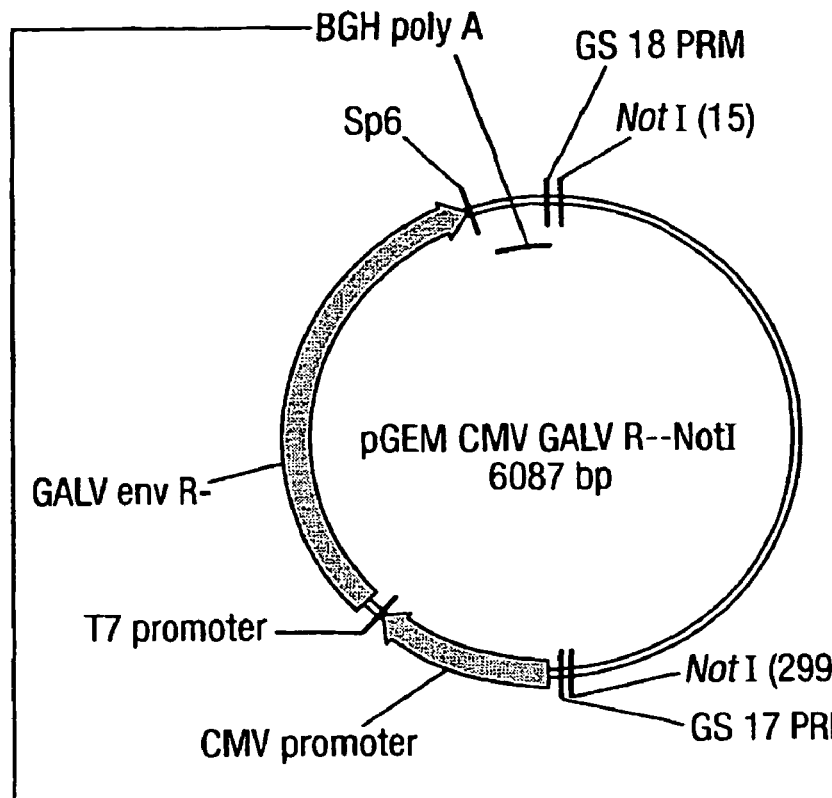
FIG. 1f shows the subcloning of GALV env R− from pGEM T Easy (Promega) to p-34.5 by restriction digestion (NotI). p-34.5 plasmid is based on pSP72 (Promega) and contains two flanking regions either side of HSV-1 ICP 34.5 gene (based on HSV-117+strain (123462-124958 bp, 125713-126790 bp)) Genbank X14112).
Figure 1F:
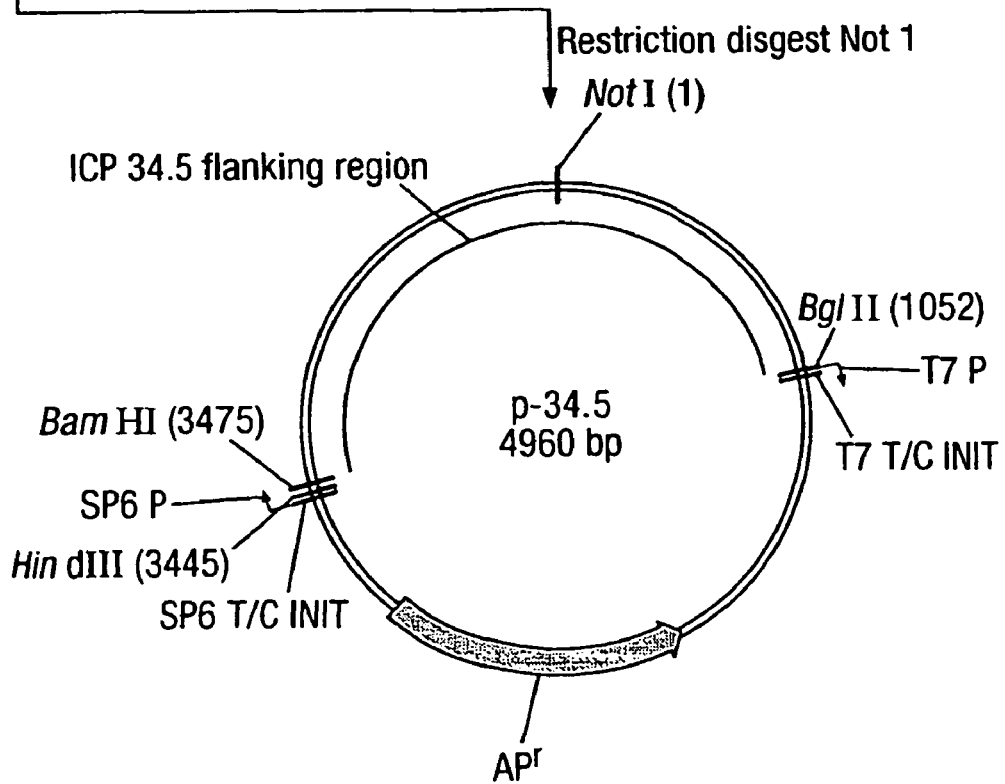
Figure 1G:
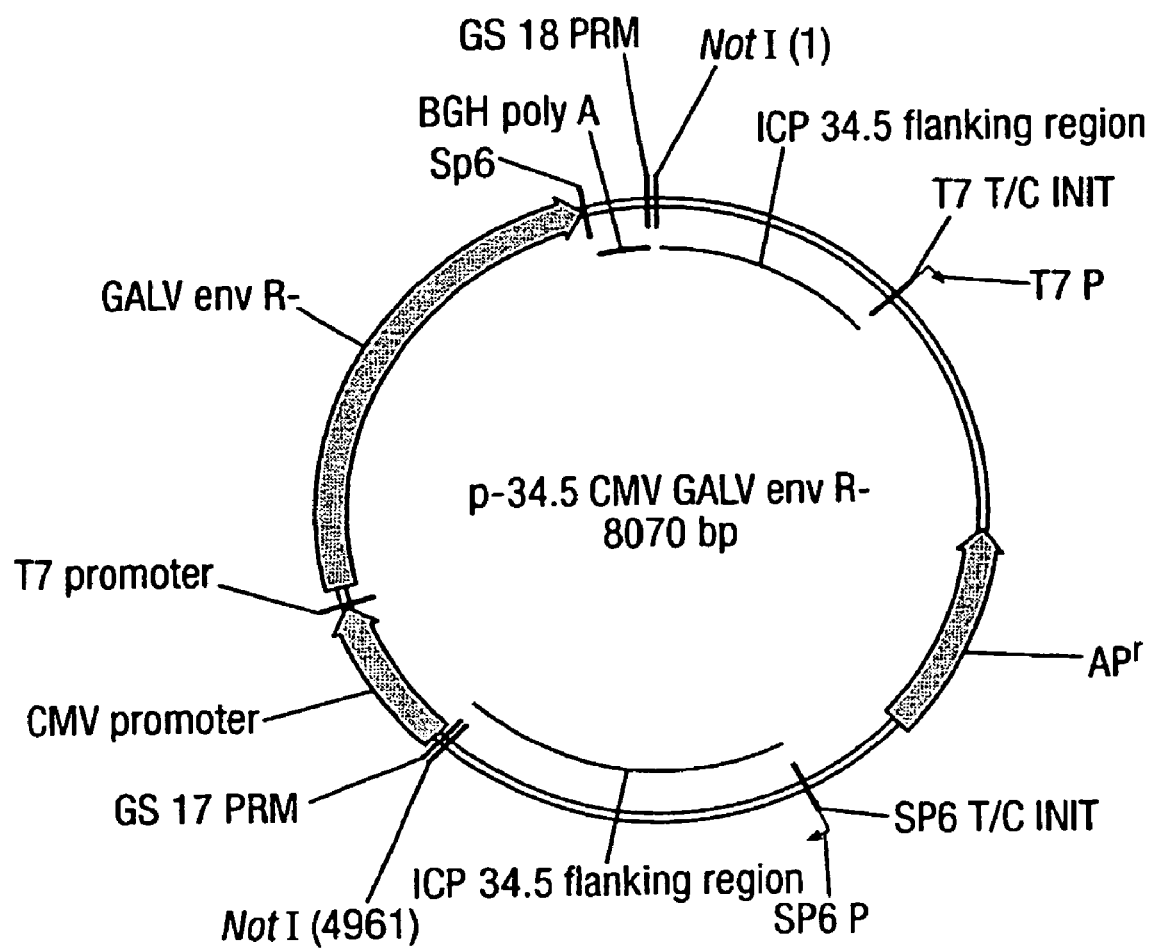
FIG. 1g shows the final shuttle vector containing ICP34.5 flanking regions (based on HSV-117+strain (123462-124958 bp, 125713-126790 bp) Genbank X14112)) and expressing the truncated envelope (env) of Gibbon Ape Leukaemia virus (Genbank NC_001885, 5552-7555 bp) under a CMV promoter and BGH poly A (Invitrogen).
Figure 1H:
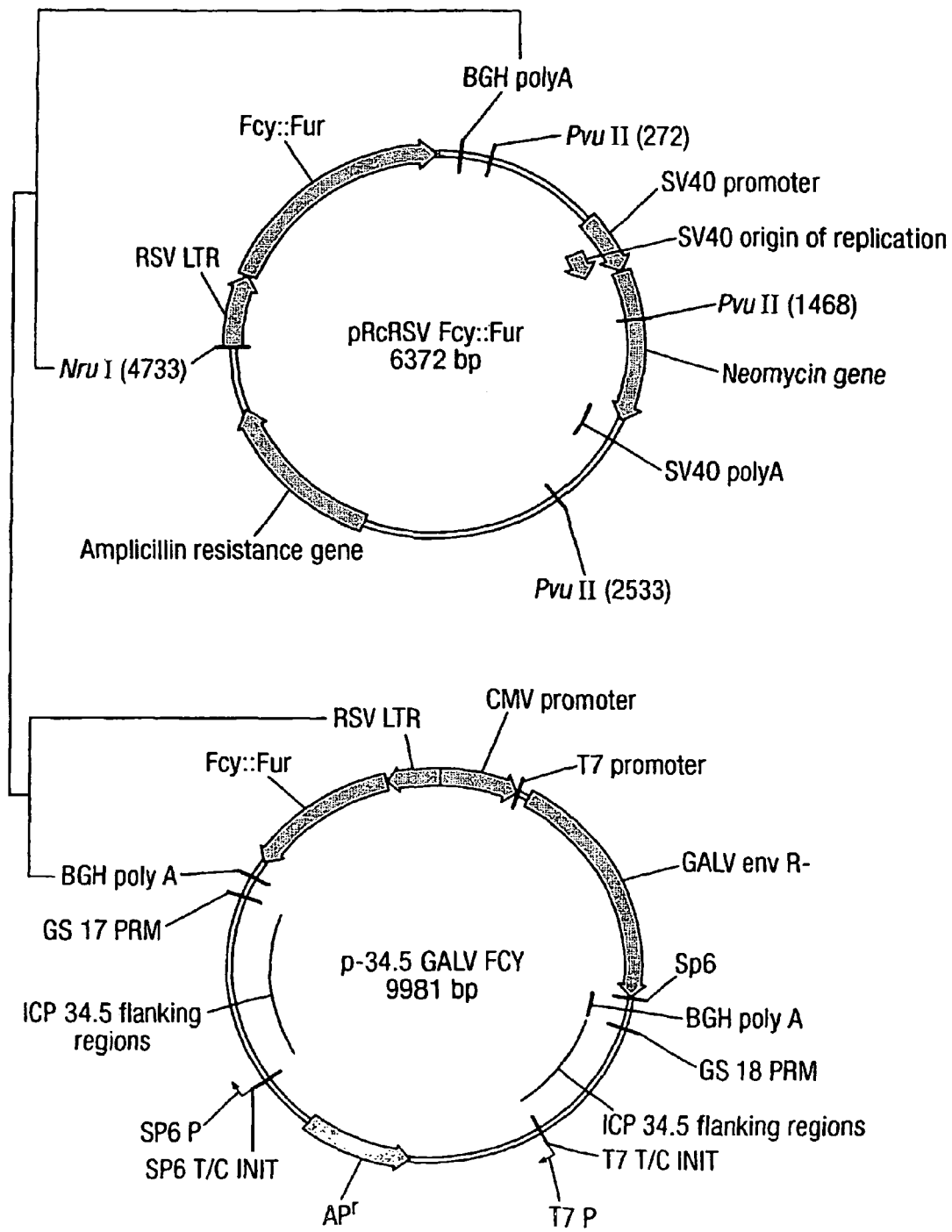
FIG. 1h shows the subcloning of RSV Fcy:Fur pA cassette from pRcRSV into p-34.5 GALV (**) by restriction digestion (Pvu II, NruI). This fragment was then ligated into the shuttle vector p-34.5 GALV cut with Nru I. p-34.5 plasmid is based on pSP72 (Promega) and contains two flanking regions either side of HSV-1 ICP 34.5 gene (based on HSV-117+strain (123462-124958 bp, 125713-126790 bp)) Genbank X14112) and expressing the truncated envelope (env) of Gibbon Ape Leukaemia virus (Genbank NC_001885, 5552-7555 bp) under a CMV promoter and BGH poly A (Invitrogen).

A herpes virus of the invention is capable of efficiently infecting target tumor cells. The genes encoding ICP34.5 are inactivated in the virus. Mutation of ICP34.5 allows selective oncolytic activity. Suitable mutations in the ICP34.5 genes are described in Chou et al 1990 and Maclean et al 1991, although any mutation which renders ICP34.5 is non-functional may be used. The genes encoding ICP47, ICP6 and/or thymidine kinase may additionally be inactivated, as may other genes if such inactivation does significantly reduce the oncolytic effect, or if such deletion enhances oncolytic or other desirable properties of the virus. Where the gene encoding ICP47 is mutated it may be mutated in such a fashion that the nearby US11 gene is expressed at earlier times in the HSV replication cycle than is usually the case. Such a mutation is described in Liu et al 2003. Viruses of the invention additionally encode two or more of a prodrug activating enzyme, a protein capable of causing cell to cell fusion and an immunomodulatory protein.

The terminology used herein for the herpes virus genes is that commonly used for genes of HSV. Where the herpes virus of the invention is from a non-HSV herpes virus the functional equivalent of each of the mentioned HSV genes is inactivated. A non-HSV gene which is a functional equivalent of an HSV gene perfoms the same function as the HSV gene and shares a degree of sequence homology with the HSV gene. The functional equivalent may be at least 30%, for example at least 40% or at least 50%, homologous to the HSV gene. Homology may be determined as described below.

Viral regions altered for the purposes described above may be either eliminated (completely or partly), or made non-functional, or substituted by other sequences, in particular by a gene encoding a prodrug converting enzyme, a gene encoding a protein capable of causing cell to cell fusion or a gene encoding an immunomodulatory protein.

The virus of the invention may be derived from a herpes simplex virus HSV strain. The HSV strain may be an HSV1 or HSV2 strain, or a derivative thereof, and is preferably HSV1. Derivatives include inter-type recombinants containing DNA from HSV1 and HSV2 strains. Such inter-type recombinants are described in the art, for example in Thompson et al 1998 and Meignier et al 1988. Derivatives preferably have at least 70% sequence homology to either the HSV1 or HSV2 genome, more preferably at least 80%, even more preferably at least 90 or 95%. More preferably, a derivative has at least 70% sequence identity to either the HSV1 or HSV2 genome, more preferably at least 80% identity, even more preferably at least 90%, 95% or 98% identity.

For example the UWGCG Package provides the BESTFIT program which can be used to calculate homology (for example used on its default settings) (Devereux et al. (1984) *Nucleic Acids Research* 12, p 387-395). The PILEUP and BLAST algorithms can be used to calculate homology or line up sequences (typically on their default settings), for example as described in Altschul (1993) J. Mol. Evol. 36:290-300; Altschul et al. (1990) J. Mol. Biol. 215:403-10.

Software for performing BLAST analyses is publicly available through the National Centre for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al., 1990). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci.* USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

A derivative may have the sequence of a HSV1 or HSV2 genome modified by nucleotide substitutions, for example from 1, 2 or 3 to 10, 25, 50 or 100 substitutions. The HSV1 or HSV2 genome may alternatively or additionally be modified by one or more insertions and/or deletions and/or by an extension at either or both ends.

Virus strains of the invention may be "non-laboratory" strains. These can also be referred to as "clinical" strains. A person of skill in the art will readily be able to distinguish between a laboratory strain and a non-laboratory, or clinical, strain. Further guidance on the properties likely to be exhibited by virus strains is given below.

The key distinction between a laboratory and non-laboratory strain is that laboratory strains currently in common use have been maintained for long periods, many years in some cases, in culture. All laboratory HSV strains will originally have been isolated from infected individuals and so are derived from clinical strains. The culture of viruses such as HSV involves a technique known as serial passage. To grow and maintain viruses, suitable cells are infected with the virus, the virus replicates within the cell and the virus is then harvested; fresh cells are then re-infected, this process constitutes one cycle of serial passage. Each such cycle may take, for example, a few days in the case of HSV. As discussed above, such serial passaging may lead to changes in the properties of the virus strain, in that selection takes places for properties that favour growth in culture (e.g. rapid replication), as opposed to properties useful for practical applications, e.g. maintenance of the capacity to travel along axons in the case of HSV or to infect human cells.

Laboratory strains in current use include HSV-1 strain F, HSV-1 strain 17+ and HSV-1 strain KOS. Non-laboratory strains useful in the invention typically have improved oncolytic activity compared to HSV-1 strains F, 17+ and KOS strains with equivalent modifications.

A non-laboratory strain is one that has been recently isolated from an infected individual. A non-laboratory strain of the present invention is a recently isolated strain that has been modified so that the gene encoding ICP34.5 is inactivated such that a functional ICP34.5 protein cannot be expressed and to include a gene encoding a pro-drug activating protein, a gene encoding a protein capable of causing cell fusion and/or an immunomodulatory protein. A virus of the invention will have spent some time in culture in order to allow the necessary modifications to be made, but any time spent in culture will be comparatively short. The clinical isolate may have been frozen for storage prior to modification, or may be frozen after modifications have been made. Strains of the invention are prepared in such a manner so as to retain substantially the desirable properties of the original clinical isolates from which they are derived.

A virus strain of the invention is derived from a parental virus strain if the parental virus strain is mutated to produce the virus. For example, a virus of the invention may be derived from the clinical isolate JS1. The parental strain of such a JS1-derived virus may be JS1 or another HSV1 strain derived from JS1. Thus a virus of the invention may be a JS1 virus which lacks a functional ICP34.5 encoding gene and which comprises two or more of a gene encoding a prodrug converting enzyme, a gene encoding a protein capable of causing cell to cell fusion and a gene encoding an immunomodulatory protein. In addition, such a virus may contain any other mutation, for example, as mentioned herein.

A virus of the invention is capable of efficiently infecting target human cancer cells. When such a virus is a non-laboratory or clinical strain it will have been recently isolated from an HSV infected individual and then screened for the desired ability of enhanced replication, infection or killing of tumour and/or other cells in vitro and/or in vivo in comparison to standard laboratory strains such as HSV-1 strains F, KOS and 17+. Such viruses of the invention with improved properties as compared to laboratory virus strains are then engineered such that they lack functional a ICP34.5 gene and encode two or more of the following genes: a gene for a prodrug activating enzyme, a gene for a protein capable of causing cell to cell fusion and a gene encoding an immunomodulatory protein wherein said genes are under the control of a suitable promoter(s). A virus strain has been recently isolated if it has undergone three years or less in culture since isolation of the unmodified clinical parent strain from its host. More preferably, the strain has undergone one year or less in culture, for example nine months or less, six months or less, three months or less, two months or less, one month or less, two weeks or less, or one week or less. By these definitions of time in culture, is meant time actually spent in culture. Thus, for example, it is a common practice to freeze virus strains in order to preserve them. Evidently, preserving by freezing or in an equivalent manner does not qualify as maintaining the strain in culture. Thus, time spent frozen or otherwise preserved is not included in the above definitions of time spent in culture. Time spent in culture is typically time actually spent undergoing serial passage, i.e. time during which selection for undesirable characteristics can occur.

Preferably, a non-laboratory virus strain has undergone 1,000 or less cycles or serial passage since isolation of its unmodified clinical precursor strain from its host. More preferably, it has undergone 500 or less, 100 or less, 90 or less, 80 or less, 70 or less, 60 or less, 50 or less, 40 or less, 30 or less, 20 or less, 10 or less, 5 or less, 4 or less, 3 or less, 2 or 1 such cycles.

Preferably, a non-laboratory virus has a greater ability, as measured by standard statistical tests, than a reference laboratory strain with the equivalent modifications to perform certain functions useful in the application at hand. In the case of an oncolytic virus for tumour treatment, a non-laboratory virus strain of the invention will preferably have a greater ability than a reference laboratory strain with equivalent modifications to infect or replicate in tumour cells, to kill tumour cells or to spread between cells in tissue. More preferably, such greater ability is a statistically significantly greater ability. For example, according to the invention, a non-laboratory strain of the invention may have up to 1.1 fold, 1.2 fold, 1.5 fold, 2 fold, 5 fold, 10 fold, 20 fold, 50 fold, or 100 fold the capacity of the reference strain in respect of the property being tested. Preferably, the reference strain is selected from HSV-1 strain 17+, HSV-1 (F) and HSV-1 KOS.

Statistical analysis of the properties described herein may be carried out by standard tests, for example, t-tests, ANOVA, or Chi squared tests. Typically, statistical significance will be measured to a level of $p=0.05$ (5%), more preferably $p=0.01p$, $p=0.001$, $p=0.0001$, $p=0.000001$.

Viruses of the invention infect and replicate in tumour cells, subsequently killing the tumour cells. Thus, such viruses are replication competent. Preferably, they are selectively replication competent in tumour cells. This means that either they replicate in tumour cells and not in non-tumour cells, or that they replicate more effectively in tumour cells than in non-tumour cells. For example, where the virus is used for treating a tumor in the central nervous system, the virus is capable of replicating in the tumor cells but not in the surrounding neuronal cells. Cells in which the virus is able to replicate are permissive cells. Measurement of selective replication competence can be carried out by the tests described herein for measurement of replication and tumour cell-killing capacity, and also analysed by the statistical techniques mentioned herein if desired.

The properties of the virus strain in respect of tumour cells can be measured in any manner known in the art. For example, the capacity of a virus to infect a tumour cell can be quantified by measuring the dose of virus required to measure a given percentage of cells, for example 50% or 80% of cells. The capacity to replicate in a tumour cell can be measured by growth measurements such as those carried out in the Examples, e.g. by measuring virus growth in cells over a period of 6, 12, 24, 36, 48 or 72 hours or longer.

The ability of a virus to kill tumour cells can be roughly quantitated by eye or more exactly quantitated by counting the number of live cells that remain over time for a given time point and MOI for given cell type. For example, comparisons may be made over 24, 48 or 72 hours and using any known tumour cell type. In particular, HT29 colorectal adenocarcinoma, LNCaP.FGC prostate adenocarcinoma, MDA-MB-231 breast adenocarcinoma, SK-MEL-28 malignant melanoma or U-87 MG glioblastoma astrocytoma cells can be used. Any one of these cell types or any combination of these cell types can be used, as may other tumour cell types. It may be desirable to construct a standard panel of tumour cell types for this purpose. To count the number of live cells remaining at a given time point, the number of trypan blue-excluding cells (i.e. live cells) can be counted. Quantitation may also be carried out by fluorescence activated cell sorting (FACS) or MTT assay. Tumour cell-killing ability may also be measured in vivo, e.g. by measuring the reduction in tumour volume engendered by a particular virus.

In order to determine the properties of viruses of the invention, it will generally be desirable to use a standard laboratory reference strain for comparison. Any suitable standard laboratory reference strain may be used. In the case of HSV, it is preferred to use one or more of HSV1 strain 17+, HSV1 strain F or HSV1 strain KOS. The reference strain will typically have equivalent modifications to the strain of the invention being tested. Thus, the reference strain will typically have equivalent modifications, such as gene deletions and heterologous gene insertions. In the case of a virus of the invention, where the ICP34.5 encoding genes have been rendered non-functional, the ICP34.5 encoding genes will also have been rendered non-functional in the reference strain. The modifications made to the reference strain may be identical to those made to the strain of the invention. By this, it is meant that the gene disruptions in the reference strain will be in exactly equivalent positions to those in the strain of the invention, e.g. deletions will be of the same size and in the same place. Similarly, in these embodiments, heterologous genes will be inserted in the same place, driven by the same promoter, etc. However, it is not essential that identical modifications be made. What is important is that the reference gene has functionally equivalent modifications, e.g. that the same genes are rendered non-functional and/or the same heterologous gene or genes is inserted.

B. Methods of Mutation

The various genes referred to may be rendered functionally inactive by several techniques well known in the art. For example, they may be rendered functionally inactive by deletion(s), substitution(s) or insertion(s), preferably by deletion. Deletions may remove one or more portions of the gene or the entire gene. For example, deletion of only one nucleotide may be made, resulting in a frame shift. However, preferably a larger deletion(s) is made, for example at least 25%, more preferably at least 50% of the total coding and non-coding sequence (or alternatively, in absolute terms, at least 10 nucleotides, more preferably at least 100 nucleotides, most preferably, at least 1000 nucleotides). It is particularly preferred to remove the entire gene and some of the flanking sequences. Where two or more copies of the gene are present in the viral genome it is preferred that both copies of the gene are rendered functionally inactive.

Mutations are made in the herpes viruses by homologous recombination methods well known to those skilled in the art. For example, HSV genomic DNA is transfected together with a vector, preferably a plasmid vector, comprising the mutated sequence flanked by homologous HSV sequences. The mutated sequence may comprise a deletion(s), insertion(s) or substitution(s), all of which may be constructed by routine techniques. Insertions may include selectable marker genes, for example lacZ or green fluorescent protein (GFP), which may be used for screening recombinant viruses, for example, β-galactosidase activity or fluorescence.

C. Heterologous Genes and Promoters

The viruses of the invention carry a two or more of a heterologous gene encoding a prodrug activating enzyme, a heterologous gene encoding a protein capable of causing cell to cell fusion and a heterologous gene encoding an immunomodulatory protein. Preferably a virus of the invention comprises a heterologous gene encoding a prodrug activating enzyme and one or both of a heterologous gene encoding a fusogenic protein and a heterologous gene encoding an immunomodulatory protein. The fusogenic protein may also function as an immunomodulatory protein.

Preferably, the prodrug activating protein is a cytosine deaminase enzyme. Cytosine deaminase genes are capable of converting the inactive prodrug 5-fluorocytosine to the active drug 5-flurouracil. Various cytosine deaminase genes are available including those of bacterial origin and of yeast origin. A second gene, typically a gene encoding a second enzyme, may be used to enhance the prodrug conversion activity of the cytosine deaminase gene. For example, the second gene may encode a uracil phosphoribosyltransferase like the viruses described in FIG. 2.

Any suitable fusogenic gene encoding a protein capable of causing cell cell fusion may be used. Preferably the protein capable of causing cell to cell fusion is selected from a modified retroviral envelope glycoprotein, such as an envelope glycoprotein derived from gibbon ape leukaemia virus (GALV) or human endogenous retrovirus W, a fusogenic F or H protein from measles virus and the vesicular stomatitis virus G protein. More preferably, the protein capable of causing cell to cell fusion is a GALV fusogenic glycoprotein.

The immunomodulatory gene may be any gene encoding a protein that is capable of modulating an immune response. The protein capable of modulating an immune response may be a cytokine, such as GM-CSF, TNF-α, an interleukin (for example IL12), a chemokine such as RANTES or a macrophage inflammatory protein (for example MIP-3) or another immunomodulatory molecule such as B7.1, B7.2 or CD40L The protein capable of causing cell to cell fusion may also be capable of modulating an immune response. For example, GALV is capable of modulating an immune response.

Viruses of the invention may thus be used to deliver the genes to a cell in vivo where they will be expressed.

The prodrug activating gene, the gene encoding a protein capable of causing cell to cell fusion and/or the gene encoding an immunomodulatory protein may be inserted into the viral genome by any suitable technique such as homologous recombination of HSV strains with, for example, plasmid vectors carrying the gene flanked by HSV sequences. The genes may be inserted at the same site in the HSV genome, for example so as to replace the ICP34.5 encoding gene, or at different sites. The genes may be expressed from separate promoters, for example a CMV promoter and an RSV promoter or from a single promoter. Where the genes are expressed from a single promoter, the genes may be separated by an internal ribosome entry site (IRES). The genes may also be expressed as a translational fusion such that the fused protein retains both activities of the separate genes (ie prodrug activation and cell to cell fusion, prodrug activation and immunomodulatory activity or cell to cell fusion and immunomodulatory activity) such that the fused proteins are cleaved following expression by a protease either in cis or in trans to the fused protein. In a preferred embodiment, the two proteins, or two of the three proteins, are expressed from an RSV and a CMV promoter respectively placed in a back-to-back orientation with respect to each other and inserted into the HSV genome so as to replace the genes encoding ICP34.5. Such a virus is described in FIG. 2. However, the gene may be inserted into the viral genome at any location(s) provided that oncolytic properties are retained.

The transcribed sequences of the inserted genes are preferably operably linked to control sequences permitting expression of the genes in a tumour cell. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequence.

A control sequence typically comprises a promoter allowing expression of the gene operably linked thereto and signal for termination of transcription. The promoter is selected from promoters which are functional in mammalian, preferably human tumour cells. The promoter may be derived from promoter sequences of a eukaryotic gene. For example, the promoter may be derived from the genome of a cell in which expression of the heterologous gene is to occur, preferably a mammalian tumour cell, more preferably a human tumour cell. With respect to eukaryotic promoters, they may be promoters that function in a ubiquitous manner (such as promoters of β-actin, tubulin) or, alternatively, in a tumour-specific manner. They may also be promoters that respond to specific stimuli, for example promoters that bind steroid hormone receptors. Viral promoters may also be used, for example the Moloney murine leukaemia virus long terminal repeat (MMLV LTR) promoter or other retroviral promoters such as that derived from Rous sarcoma virus (RSV), the human or mouse cytomegalovirus (CMV) IE promoter or promoters of herpes virus genes including those driving expression of the latency associated transcripts.

Expression cassettes and other suitable constructs comprising the prodrug converting enzyme encoding gene, gene encoding a protein capable of promoting cell to cell fusion and/or immunomodulatory gene and control sequences can be made using routine cloning techniques known to persons skilled in the art (see, for example, Sambrook et al., 1989, Molecular Cloning—A laboratory manual; Cold Spring Harbor Press).

It may also be advantageous for the promoter(s) to be inducible so that the levels of expression of the genes can be regulated during the life-time of the tumour cell. Inducible means that the levels of expression obtained using the promoter can be regulated. For example, a virus of the invention may further comprise a heterologous gene encoding the tet repressor/VP16 transcriptional activator fusion protein under the control of a strong promoter (e.g. the CMV IE promoter) and the prodrug converting, cell to cell fusion or immunomodulatory or other gene may be under the control of a promoter responsive to the tet repressor VP16 transcriptional activator fusion protein previously reported (Gossen and Bujard, 1992, Gossen et al, 1995). Thus, in this example, expression of the gene(s) would depend on the presence or absence of tetracycline.

Viruses of the invention encode multiple heterologous genes. Viruses of the invention may comprise one or more additional genes, for example from 1, 2 to 3, 4 or 5 additional genes. The additional gene(s) may be further copies of the prodrug converting gene, the fusiogenic gene and/or the immunomodulatory gene. The additional gene(s) may encodes one or more different prodrug converting gene, one or more different fusiogenic gene and/or one or more different immunomodulatory gene. The additional gene(s) may encodes other gene(s) intended to enhance the therapeutic effect.

More than one gene and associated control sequences could be introduced into a particular HSV strain either at a single site or at multiple sites in the virus genome. Alternatively pairs of promoters (the same or different promoters) facing in opposite orientations away from each other, each driving the expression of a gene may be used.

D. Therapeutic Uses

Viruses of the invention may be used in a method of treating the human or animal body. In particular, viruses of the invention may be used in methods of cancer therapy. Preferably, viruses of the invention are used in the oncolytic treatment of cancer. Viruses of the invention may be used in the therapeutic treatment of any solid tumour in a mammal, preferably a human. For example viruses of the invention may be administered to a subject with prostate, breast, lung, liver, renal cell, endometrial, bladder, colon or cervical carcinoma; adenocarcinoma; melanoma; lymphoma; glioma; sarcomas such as soft tissue and bone sarcomas; or cancer of the head and neck.

E. Administration

The viruses of the invention may be used in a patient, preferably a human patient, in need of treatment. A patient in need of treatment is an individual suffering from cancer, preferably an individual with a solid tumour. The aim of therapeutic treatment is to improve the condition of a patient. Typically therapeutic treatment using a virus of the invention allieviates the symptoms of the cancer. A method of treatment of cancer according to the invention comprises administering a therapeutically effective amount of a virus of the invention to a patient suffering from cancer. Administration of an oncolytic virus of the invention to an individual suffering from a tumour will typically kill the cells of the tumour thus decreasing the size of the tumour and/or preventing spread of malignant cells from the tumour.

One method of administering therapy involves combining the virus with a pharmaceutically acceptable carrier or diluent to produce a pharmaceutical composition. Suitable carriers and diluents include isotonic saline solutions, for example phosphate-buffered saline.

Therapeutic treatment may be carried out following direct injection of the virus composition into target tissue. The target tissue may be the tumour or a blood vessel supplying the tumour. The amount of virus administered is in the case of HSV in the range of from $10^4$ to $10^{10}$ pfu, preferably from $10^5$ to $10^8$ pfu, more preferably about $10^6$ to $10^9$ pfu. Typically 1-4 ml, such as 2 to 3 ml of a pharmaceutical composition consisting essentially of the virus and a pharmaceutically acceptable suitable carrier or diluent would be used for direct injection into an individual tumour. However for some oncolytic therapy applications larger volumes up to 10 ml may also be used, depending on the tumour type, tumour size and the inoculation site. Likewise, smaller volumes of less than 1 ml may also be used.

The routes of administration and dosages described are intended only as a guide since a skilled practitioner will be able to determine readily the optimum route of administration and dosage. The dosage may be determined according to various parameters, especially according to the location of the tumour, the size of the tumour, the age, weight and condition of the patient to be treated and the route of administration. Preferably the virus is administered by direct injection into the tumour. The virus may also be administered systemically or by injection into a blood vessel supplying the tumour. The optimum route of administration will depend on the location and size of the tumour.

THE FOLLOWING EXAMPLES ILLUSTRATE THE INVENTION

In work aimed at producing ICP34.5 deleted HSV with enhanced oncolytic and anti-tumour potential, we have deleted ICP47 and ICP34.5 from HSV1 strain JS1 and have inserted the genes encoding a prodrug activating gene (a cytosine deaminase/uracil phosphoribosyltransferase fusion gene) and/or a gene for a GALV fusogenic glycoprotein.

Example 1

Figure 2:
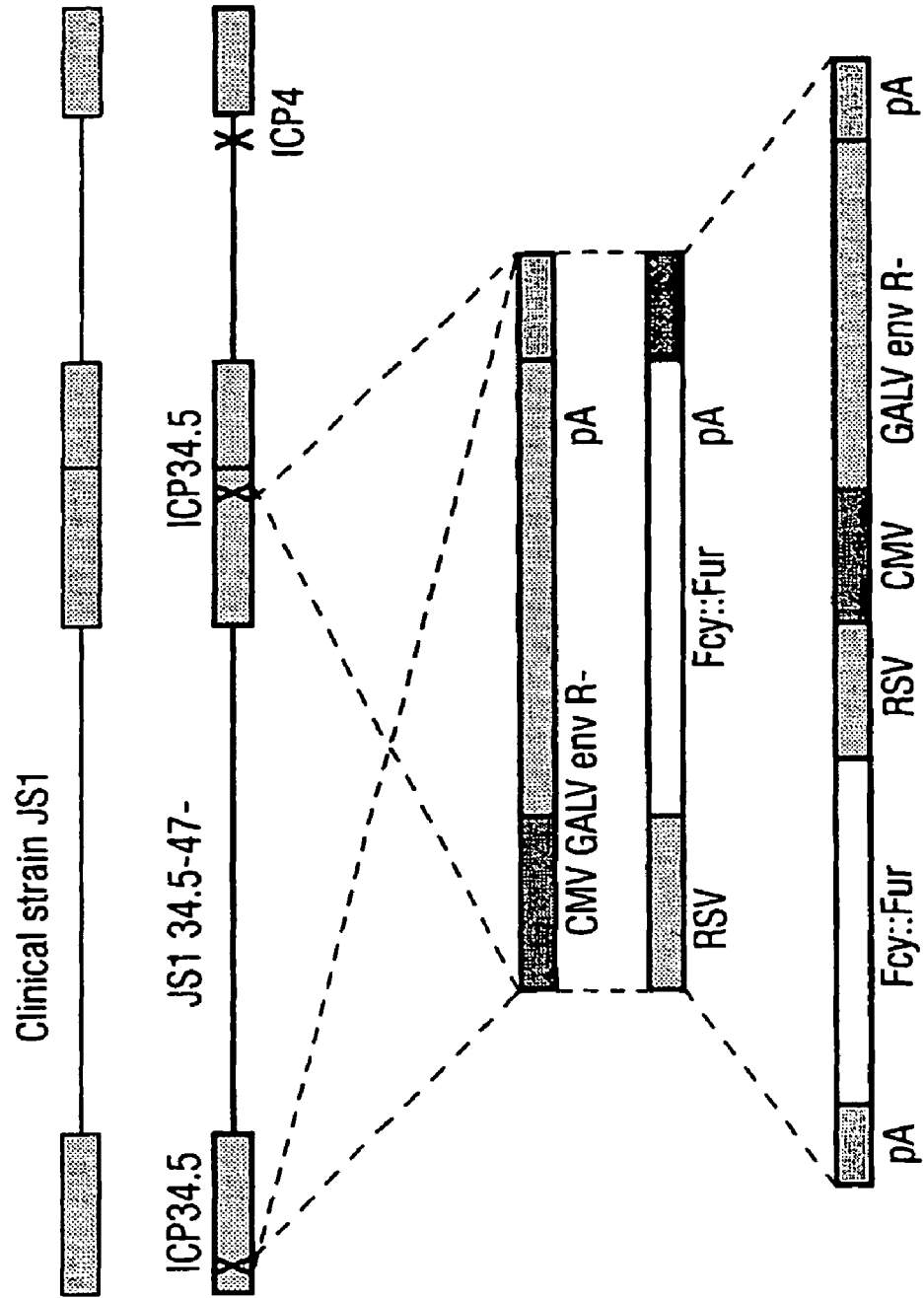
FIG. 2 is a schematic representation of virus vectors used in this study. HSV-1 strain JS1 was isolated by taking a swab from a cold sore of a otherwise healthy volunteer (Liu et al 2003). JS1/34.5−/47− has two deletions. The first involves removal of the coding region of the ICP34.5 gene (nucleotides 124948-125713 based on the sequence HSV-1 strain 17+). The second involves a 280 bp deletion of ICP47 (nucleotides 145570-145290 based on the sequence HSV-1 strain 17+) (Liu et al 2003). JS1/34.5−/GALVenv R−/47− expresses the retroviral envelope of gibbon ape leukaemia virus—the R-peptide (Genbank NC_001885, 5552-7555 bp) (Bateman et al 2000, Galanis et al 2001) under CMV promoter. JS1/34.5−/RSV/Fcy:Fur/47− expresses the enzyme prodrug activator yeast cytosine deaminase fusion to uracil phospo-ribosyltransferase (Invivogen) under RSV promoter. JS1/34.5−/GALV/env R−/Fcy:Fur/47− combines both fusogenic retroviral envelope and enzyme prodrug activator.

Virus Construction (see FIGS. 1 & 2)

The viruses used were based on the clinical, or "non-laboratory", HSV1 strain, JS1. ICP34.5 and ICP47 were completely deleted from strain JS1. This virus is described in Lui et al 2003. The GALV env R− (Bateman et al 2000, Galanis et al 2001) and/or the cytosine deaminase/uracil phosphoribosyltransferase fusion gene (Fcy:Fur; Invitrogen) were then inserted in place of the ICP34.5 encoding gene under CMV and RSV promoter control respectively.

FIGS. 1a-1h demonstrate the stepwise construction of the plasmids used to construct the viruses:

Step 1 (FIG. 1a): The Fcy::Fur gene was excised from pORF Fcy::Fur with NcoI and NheI and inserted into pRCRSV following digestion with HindIII and XbaI;

Step 2 (FIG. 1b): The RSV promoter/Fcy::Fur/BGHpA cassette from PRcRSV Fcy::Fur was inserted between ICP34.5 flanking regions (Lui et al 2003) to generate p-34.5 Fcy::Fur;

Step 3 (FIG. 1c): The GALV env R− was amplified by PCR from cells containing the integrated provirus and cloned into pcDNA3 between the NotI and EcoRI sites to generate pcDNA3 kGALV env R−;

Step 4 (FIG. 1d-1e): Manipulation to remove restriction sites which were not required;

Step 4 (FIG. 1g): The CMV promoter/GALV R−/BGHpA cassette was cloned into ICP34.5 flanking regions to generate p-34.5 CMV GALV env R−;

Step 5 (FIG. 1h): To generate a plasmid allowing insertion in place of ICP34.5 and containing both GALV env R− and Fcy::Fur genes, the RSV promoter/Fcy::Fur/pA cassette from pRcRSV Fcy::Fur was excised and inserted into p-34.5 CMV GALV env R− to generate p-34.5 GALV FCY.

Plasmids p-34.5 Fcy::Fur, p-34.5 CMV GALV env R− and p-34.5 GALV FCY were inserted into virus strain JS1/34.5−/47− CMV GFP (Lui et al 2003) by homologous recombination so as to replace the GFP sequence replacing ICP34.5. Recombinant, non-GFP expressing plaques were selected generating three viruses (JS1/34.5−/47−/Fcy::Fur, JS1/34.5−/47−/GALV and JS1/34.5−/47−/Fcy::Fur). These are shown in FIG. 2.

Example 2

The GALV env R− Expressing Viruses Mediate Cell to Cell Fusion

The GALV alone expressing virus (i) causes cell to cell fusion of a number of human tumour cell lines in vitro, including HT1080, Fadu and U87MG, mediated by the expression of the GALV protein, and (ii) provides increased anti-tumour activity in vivo in mouse models (Fadu and HT1080) as compared to the equivalent virus not expressing the GALV protein.

Figure 3A:
FIG. 3 shows the fusion of tumour cells by GALV env R−. A plaque is shown of JS1/34.5−/47− (A) and JS1/34.5−/47−/GALV (B) following infection of rat RG2 cells and staining with crystal violet.
Figure 3B:
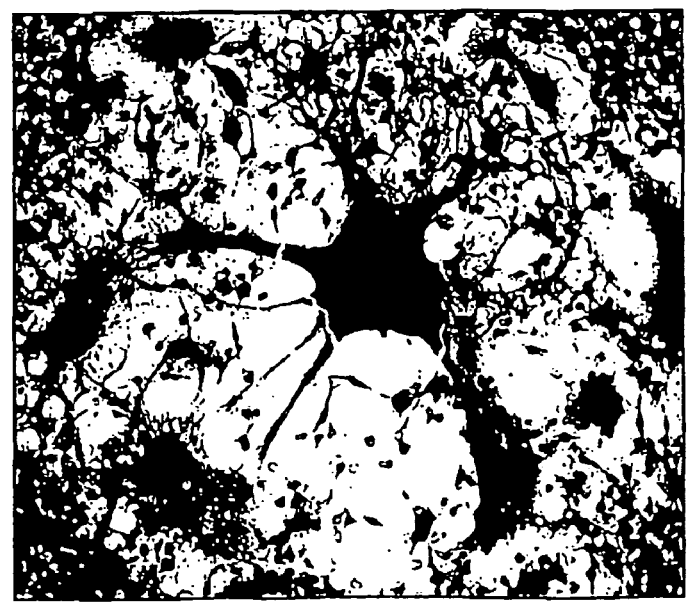

Cell to cell fusion is demonstrated in FIG. 3. Rat RG2 glioma cells were infected either with JS1/34.5−/47− or JS1/34.5−/47−/GALV and effects on plaque morphology observed. It can be seen that the GALV expressing virus produces greatly enlarged plaques with signs of a syncitial (cell to cell fusion) effect easily being observed.

Example 3

The Fcy::Fur Expressing Viruses Demonstrate Cytosine Deaminase Activity

Figure 4:
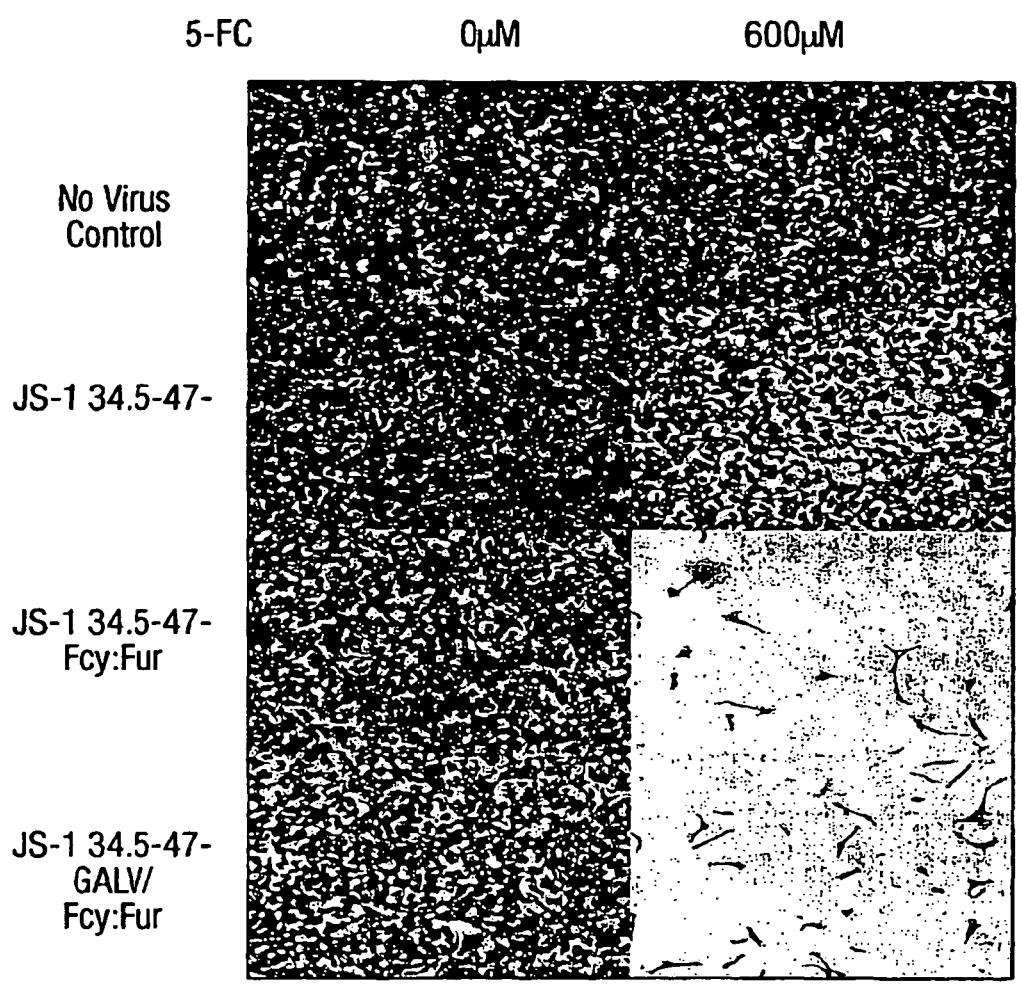
FIG. 4 shows the effect of supernatant from HT1080 cells 48 hours after infection with the control virus, JS1/34.5−/47−, JS1/34.5−/47−/Fcy:Fur or JS1/34.5−/47−/GALV/Fcy:Fur, in the presence or absence of 5-fluorocytosine (5-FC). These supernatants were then heat inactivated and then added to fresh HT1080 cells for 72 hours. The two lower right hand panels show near complete cell death indicating that 5-fluorocytosine has been converted to 5-fluorouracil by the Fcy:Fur containing viruses.

The cytosine deaminase/uracil phosphoribosyltransferase fusion gene containing virus has demonstrated that it directs the conversion of 5-fluorocytosine to 5-fluorouracil in vitro such that 5-fluoruracil mediated cell killing occurs. This is shown in FIG. 4 where HT1080 cells were infected with the three viruses in the presence or absence of 5-fluorocytosine. Supernatants from these cells were then heat treated to inactivate the virus present in the supernatants. These supernatants were then used to overlay new cells. If 5-fluorocytosine had been converted to the toxic 5-fluorouracil these new cells would then be killed. It can be seen from the FIG. 4 that when the virus used to infect the original HT1080 cells contained the Fcy::Fur gene, the cells onto which the resulting supernatants were overlaid were killed demonstrating the biological activity of the Fcy::Fur gene.

Example 4

Figure 5:
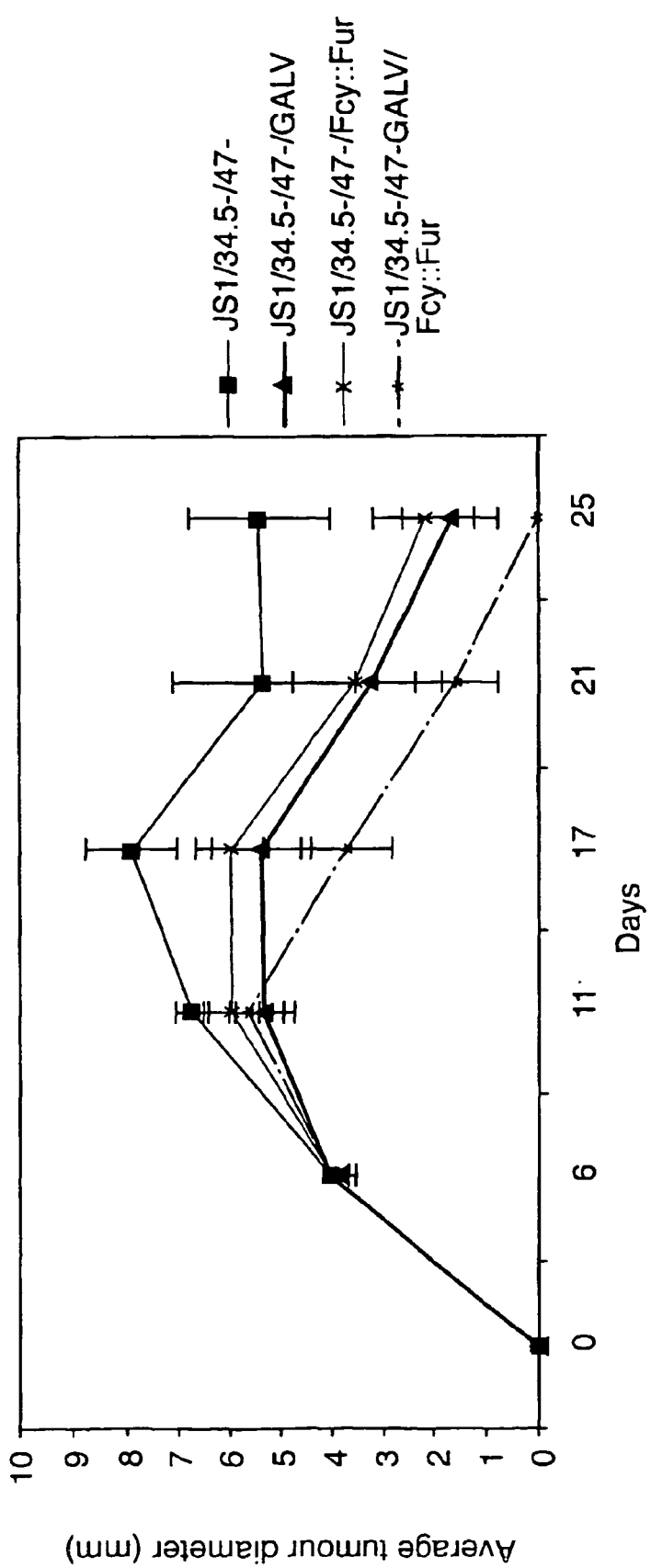
FIG. 5 shows the effect of JS1/34.5−/47−, JS1/34.5−/47−/GALV, JS1/34.5−/47−/Fcy:Fur viruses on shrinking tumours implanted in rats. Rat 9L tumour cells were implanted into the flank of Fischer rats and allowed to develop to give a tumour diameter of approx 4-5 mm. Groups of five rats were then injected with 50 μl of 1×10 esp8 pfu/ml the indicated virus, intratumorally, on days 7, 10, 13, 17 and 20. 500 mg/kg of 5-fluorocytosine was administered by the intraperitoneal route on days 9, 11, 12, 14, 16, 18, 19, 21, 23, 24, 25, 26 and tumour diameters measured. Error bars represent standard deviation.

The Combination of GALV env R− and Fcy::Fur Expression Combined with 5-fluorocytosine Expression Provides Enhanced Anti-Tumour Activity In Vivo as Compared to the Use of Either Gene Alone FIG. 5 shows the effects of three viruses (JS1/34.5−/47−/GALV, JS1/34.5/47−/Fcy::Fur and JS1/34.5−/47−/GALV/Fcy::Fur) and an 'empty vector' control (JS1/34.5−/47−) on shrinking tumours implanted in the flanks of rats. The viruses were administered in combination with 5-fluorocytosine. It can be seen from FIG. 5 that each of the viruses causes shrinkage of the injected tumours. However, while delivery of either GALV env R− or Fcy::Fur alone gives improved tumour shrinkage as compared to the empty vector control, the combined delivery of both GALV env R− and Fcy::Fur gives still further improved tumour shrinkage effects, with all tumours in this case being cured. It can be concluded, therefore, that co-delivery of a pro-drug activating gene and a fusogenic glycoprotein gives improvements with respect to turnour therapy as compared to either of the approaches when used alone.

Deposit Information

HSV1 strain JS1 has been deposited at the European Collection of Cell Cultures (ECACC), CAMR, Sailsbury, Wiltshire SP4 0JG, United Kingdom, on 2 Jan. 2001 under provisional accession number 01010209.

REFERENCES

Chou et al. 1990, Science 250: 1262-1266
Maclean et al. 1991, J. Gen. Virol. 72: 631-639
Gossen M & Bujard H, 1992, PNAS 89: 5547-5551
Gossen M et al. 1995, Science 268: 1766-1769
Thompson et al. 1998, Virus Genes 1(3); 275-286
Meignier et al. 1988, Infect. Dis. 159; 602-614
Liu et al et al 2003, Gene Therapy 10; 292-303
Bateman et al 2000, Cancer Research 60; 1492-1497
Galanis et al 2001, Human Gene Therapy 12; 811-821

The invention claimed is:

1. A herpes simplex virus which is modified such that it lacks a functional ICP34.5 encoding gene, which is derived from HSV1 JS1 as deposited at the European collection of cell cultures (ECAAC) under accession number 01010209 and which comprises:
   (i) a heterologous gene encoding a prodrug converting enzyme; and
   (ii) a heterologous gene encoding a protein capable of causing cell to cell fusion.

2. A virus according to claim 1, wherein said prodrug converting enzyme is a cytosine deaminase.

3. A virus according to claim 1, wherein said protein capable of causing cell to cell fusion is a gibbon ape leukaemia fusogenic glycoprotein.

4. A virus according to claim 1, which further comprises a heterologous gene encoding an a protein capable of enhancing an anti-tumor therapeutic effect of the virus.

5. A virus according to claim 4, wherein the protein is an immunomodulatory protein selected from group consisting of GM-CSF, TNFα and CD40L.

6. A virus according to claim 1, which further lacks a functional gene encoding ICP47.

7. A virus according to claim 1, which further lacks a functional gene encoding ICP6, glycoprotein H and/or thymidine kinase.

8. A virus according to claim 1, which further lacks a gene encoding a functional protein capable of inhibiting dendritic cell function.

9. A virus according to claim 8, in which said gene encoding a functional protein capable of inhibiting dendritic cell function is UL43 or vhs.

10. A pharmaceutical composition comprising as active ingredient a virus according to claim 1 and a pharmaceutically acceptable carrier or diluent.

11. A method of treating a tumor in an individual in need thereof by administering to said individual an effective amount of a virus according to claim 1.

12. A method according to claim 11 wherein said virus is administered by direct intra-tumoral inoculation.

* * * * *